United States Patent [19]

Watson et al.

[11] 4,060,091

[45] Nov. 29, 1977

[54] TOBACCO AND TOBACCO-CONTAINING MANUFACTURES CONTAINING AN INGREDIENT HAVING PHYSIOLOGICAL COOLING ACTIVITY

[75] Inventors: Hugh R. Watson, Wargrave; David G. Rowsell, Staines; David John Spring, Datchet, all of England

[73] Assignee: Wilkinson Sword Limited, London, England

[21] Appl. No.: 486,565

[22] Filed: July 8, 1974

Related U.S. Application Data

[63] Continuation-in-part of Ser. No. 221,755, Jan. 28, 1972, abandoned.

[51] Int. Cl.$^2$ ............................................. A24B 3/12
[52] U.S. Cl. .................................. 131/9; 131/17 R; 131/144
[58] Field of Search ............. 131/8, 17, 9, 144, 261 A; 260/631 R; 424/343, 320, 358

[56] References Cited

U.S. PATENT DOCUMENTS 3,644,653  2/1972  Tcheiltcheff ........................ 424/358

FOREIGN PATENT DOCUMENTS 1,065,767  9/1959  Germany ......................... 131/261 A

OTHER PUBLICATIONS

Chem. Abst. Subject Index, 1947–1956, vols. 41–50, pp. 3848s–3849s.

Primary Examiner—Robert W. Michell
Assistant Examiner—V. Millin
Attorney, Agent, or Firm—Leydig, Voit, Osann, Mayer & Holt, Ltd.

[57] ABSTRACT

According to the invention physiological cooling activity is imparted to tobacco and tobacco-containing manufactures, e.g. pipe tobacco and cigarettes by incorporating therein certain cold receptor stimulating p-menthane-3-carboxamides.

10 Claims, No Drawings

TOBACCO AND TOBACCO-CONTAINING MANUFACTURES CONTAINING AN INGREDIENT HAVING PHYSIOLOGICAL COOLING ACTIVITY

RELATED APPLICATIONS

This application is a continuation-in-part of application Ser. No. 221,755, filed Jan, 28, 1972, now abandoned. It is also related to applications Serial Nos. 486,564 and 486,566 both filed on July 8, 1974.

FIELD OF INVENTION

This invention relates to tobacco and tobacco-containing manufactures containing an ingredient having a physiological cooling effect on the mucous membrances of the mouth, nose and throat when the tobacco is chewed or inhaled (as in the case of snuff) or when the smoke therefrom is inhaled, as during normal smoking.

BACKGROUND OF THE INVENTION AND PRIOR ART

Menthol is well known for its physiological cooling effect on the skin and mucous membrances of the mouth and has been extensively used as a flavouring agent in tobacco for producing a "cool" sensation in the mouth when smoking.

It is well established that the "cooling" effect of menthol is a physiological effect due to the direct action of menthol on the nerve endings of the human body responsible for the detection of hot or cold and is not due to latent heat of evaporation. It is believed that the menthol acts as a direct stimulus on the cold receptors at the nerve endings which in turn stimulate the central nervous system.

Although menthol is well established as a physiological coolant its use in tobacco is circumscribed by its strong minty odour and its relative volatility. For example, it is well known that "mentholated" cigarettes deteriorate quite rapidly on storage.

A few other compounds have been reported in the technical literature as having an odour or flavour similar to menthol and from time to time have been proposed as flavourants in tobacco. For example, Japanese Patent Publication No. 39-19627 reports that 3-hydroxymethyl p-menthane (menthyl carbinol) has a flavour closely resembling that of 1-menthol and suggests its use as a flavourant in tobacco. In Swiss Pat. No. 484,032 certain saccharide esters of menthol are proposed as additives to tobacco. Other compounds have been reported in the literature as having an odour and physiological cooling effect similar to menthol but without any specific recommendation for their use as additives in tobacco. For example, in French Patent Specification No. 1,572,332 N,N-Dimethyl 2-ethylbutanamide is reported as having a minty odour and refreshing effect, and the minty odour of N,N-diethyl 2,2-dimethylpropanamide is referred to. A similar effect is reported for N,N-diethyl 2-ethylbutanamide in Berichte 39, 1223, (1906). A minty odour has also been reported for 2,4,6-trimethylheptan-4-ol and 2,4,6-trimethyl hept-2-en-4-ol in Parfums-Cosmetiques-Savons, May 1956, pp. 17-20. The cooling effect of menthol and other related terpene alcohols and their derivatives has also been studied and reported in Koryo, 95, (1970), pp. 39-43. 2,3-p-menthane diol has also been reported as having a sharp cooling taste (Beilstein, Handbuch der Organischen Chemie, 4th Ed. (1923) Vol. 6, p. 744).

Desprite this knowledge of other compounds having an odour and flavour similar to that of menthol, menthol is still extensively used in tobacco notwithstanding the disadvantages mentioned above, namely its very strong odour and its relative volatility.

OBJECTS OF THE INVENTION

It is an object of the present invention to provide tobacco and tobacco-containing manufactures containing an ingredient which creates a "cool" sensation when the ingredient comes into contact with the nasal and oral mucosa, either in the tobacco smoke, or by direct contact of the tobacco on the nasal or oral mucosa, but which are not subject to the disadvantages of a strong minty flavour and storage instability.

It is a further object of the present invention to provide an improved method of imparting to tobacco and tobacco-containing manufactures a physiological cooling activity.

SUMMARY OF INVENTION

The present invention is based on the discovery of a group of 3-substituted-p-menthanes which have a pronounced physiological cooling activity, which have little or no odour, which are of relatively low volatility and which are substantially non-toxic. These compounds are 3-substituted-p-menthanes of the formula:

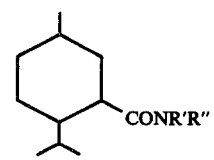

I where
R', when taken separately, is hydrogen or an aliphatic radical containing up to 25 carbon atoms;
R", when taken separately is hydroxy, or an aliphatic radical containing up to 25 carbon atoms, with the proviso that when R' is hydrogen R" may also be an aryl radical of up to 10 carbon atoms and selected from the group consisting of substituted phenyl, phenalkyl or substituted phenalkyl, naphthyl and substituted naphthyl, pyridyl; and
R' and R", when taken together with the nitrogen atom to which they are attached, represent a cyclic or heterocyclic group of up to 25 carbon atoms, e.g. piperidino, morpholino etc.

In the above definitions "aliphatic" is intended to include any straight-chained, branched-chained or cyclic radical free or aromatic unsaturation, and thus embraces alkyl, cycloalkyl, alkenyl, cycloalkenyl, alkynyl, hydroxyalkyl, acyloxyalkyl, alkoxy, alkoxyalkyl, aminoalkyl, acylaminoalkyl, carboxyalkyl and similar combinations.

Typical values for R' and R" when aliphatic are methyl, ethyl, propyl, butyl, isobutyl, n-decyl, cyclopropyl, cyclohexyl, cyclopentyl, cycloheptylmethyl, 2-hydroxyethyl, 3-hydroxy-n-propyl, 6-hydroxy-n-hexyl, 2-aminoethyl, 2-acetoxyethyl, 2-ethylcarboxyethyl, 4-hydroxybut-2-ynyl, carboxymethyl etc.

When R" is aryl typical values are benzyl, naphthyl, 4-methoxyphenyl, 4-hydroxyphenyl, 4-methylphenyl, 3-hydroxy-4-methylphenyl, 4-fluorophenyl, 4-nitrophenyl, 2-hydroxynaphthyl, pyridyl, etc.

STATEMENT OF INVENTION

According to the present invention, therefore, there are provided tobacco and tobacco-containing manufactures comprising tobacco and a cold receptor stimulating additive, present in an amount effective to stimulate the cold receptors of the nervous system of mucous membranes of the oral and nasal mucosa when the tobacco or tobacco-containing manufacture is smoked, chewed or inhaled by the human user, said additive being a cold receptor stimulating 3-substituted-p-menthane of the formula hereinbefore defined.

By tobacco and tobacco-containing manufactures we mean any article, such as a cigarette or cigar, or any composition, such as pipe or chewing tobacco or snuff, containing tobacco in a prepared form ready for utilisation by the human person whether by smoking, i.e. burning of the prepared tobacco and inhalation of the tobacco smoke, chewing or direct inhalation of the tobacco.

DETAILED DESCRIPTION

The 3-substituted-p-menthanes used as cold receptor stimulants in this invention may be readily prepared by conventional methods, such as by the reaction of the corresponding acid chloride (obtained by reacting p-menthane-3-carboxylic acid with thionyl chloride) with the appropriate mono or di-substituted amine. The reaction will usually be carried out in solution in the presence of a hydrogen chloride receptor e.g. sodium hydroxide. The reaction proceeds smoothly at room temperature. The preparation of the compounds used in this invention is more fully disclosed in our related U.S. patent application Ser. No. 486,566 to which reference should be made, and wherein 16 examples are given of specific methods for preparing the subject compounds.

The compounds used as cold receptor stimulants in accordance with this invention exhibit both geometric and optical isomerism and, depending on the starting materials and the methods used in their preparation the compounds may be isomerically pure, i.e. consisting of one geometric or optical isomer, or they may be isomeric mixtures, both in the geometric and optical sense.

As is well known, the basic p-menthane structure is a chair-shaped molecule which can exist in cis or trans forms. Substitution of the carboxyl or amide group into the 3-position gives rise to four configurational or geometric isomers depending upon whether the substitution is axially or equatorially into the cis or trans isomer, the four isomers being related as menthol is to neomenthol, isomenthol, and neoisomenthol. In general it is found that in the compounds used in this invention the equatorially substituted derivatives have the greater cooling effect than the axial compounds and are to be preferred.

Substitution of the amide group in the 3-position of the p-menthane structure also gives rise to optical isomerism, each of the above-mentioned four geometric isomers, existing in d, l and dl forms. The physiological cooling effect is found, in most cases, to be greater in the l-form than in d-form, and in some cases substantially greater. The amide derivatives of the l-acid are therefore preferred.

The cooling sensation created by the compounds used in this invention on the skin and mucous membranes, for example, in the mouth, varies both in intensity and longevity from compound to compound.

When either R' and R" is aliphatic the preferred values are $C_1$–$C_9$ straight or branched chain alkyl, $C_1$–$C_9$ straight or branced chain hydroxyalkyl or aminoalkyl and $C_1$–$C_4$ acylated derivatives thereof, and —$C_nH_{2n}$COR''' or —$C_nH_{2n}$COOR''', where —$C_nH_{2n}$ is a straight or branched chain alkylene radical in which n is an integer of from 1–6 and R''' is hydrogen or a $C_1$–$C_8$ alkyl or hydroxyalkyl group, preferably a $C_1$–$C_4$ straight chain alkyl group.

In general the monosubstituted compounds, i.e. where R' is H, are preferred although di-substituted compounds where R' and R" are both $C_1$–$C_3$ alkyl also show a very pronounced cooling effect. Most preferred of all are compounds where R' is H and R" is $C_1$–$C_3$ alkyl, $C_1$–$C_4$ hydroxyalkyl, or —$CH_2$COOR''', where R''' is $C_1$–$C_4$ alkyl.

Also included within the scope of this invention are compounds where R' is H and R" is hydroxy or substituted phenyl, e.g. alkylphenyl, hydroxyphenyl, alkoxyphenyl, halophenyl of up to 10 carbon atoms, phenalkyl or substituted phenalkyl e.g. benzyl, naphthyl or substituted naphthyl, and compounds where R' and R" are joined to form a cyclic group. When so joined R' and R" preferably represent an alkylene chain, optionally interrupted by oxygen, which together with the nitrogen atom to which R' and R" are attached forms a 5- or 6-membered heterocyclic ring.

For the purpose of the present disclosure the following test procedure has been devised as a means to identify compounds having a physiological cooling activity in accordance with the present invention and herein referred to as cold receptor stimulant. This test is intended purely as a means for identifying compounds having a physiological cooling activity and useful in the present invention and for giving an indication of the different relative activities of the compounds, as between themselves and as compared with menthol. The test is not intended as anything more than a very rough guide in the choice of cold receptor stimulant to be used in any particular tobacco or tobacco containing manufacture where other factors will come into play. For example, different compounds will be more suitable for incorporation into cigarettes, particularly if simply deposited on a filter tip, than in pipe tobacco, chewing tobacco or snuff. Similarly, different compounds will be more suited to incorporation in pipe tobacco and chewing tobacco. The formulation of actual products according to this invention will therefore be done largely on an empirical basis although the test results and other figures given herein will be useful as a guide, particularly in the formulation of chewing tobacco, since the test procedure to be described involves oral application of the compound.

It will also be noted that the described test procedure is done on a statistical basis. This is necessary since sensitivity to these compounds will vary from one individual to another. Tests of this nature are commonly used in the testing of the organoleptic properties, e.g. taste, smell, etc. of organic and inorganic compounds, see Kirk-Othmer: Encyclopedia of Chemical Technology, 2nd Ed. (1967) Vol. 14 pages 336–344.

TEST PROCEDURE

The following test procedure is aimed at determining the minimum quantity of the test compound required to produce a noticeable cooling effect on a person of average sensitivity, this minimum quantity being termed the threshold for that particular compound. The tests are carried out on a selected panel of six people of median sensitivity to 1-menthol.

PANEL SELECTION

To select a test panel of average sensitivity the following procedure is used. Known quantities of 1-menthol in solution in petroleum ether (bp. 40–60 ) are placed on 5 mm. squares of filter paper, whereafter the solvent is allowed to evaporate. A panel of observers is enrolled and asked to place one impregnated square at a time on the tongue and to report on the presence or absence of a cooling effect. The quantity of 1-menthol on each impregnated square is gradually reduced from a value substantially above 0.25 $\mu$g. per square to substantially below 0.25 $\mu$g, the precise range being immaterial. Conveniently, one starts with squares containing 2.0 $\mu$g. 1-menthol, the amount on each successive square being half that of the preceding square, i.e. the second test square will contain 1.0 $\mu$g. the third 0.5 $\mu$g and so on. Each quantity is tested on the tongue at least 10 times. In this way, the thresholds to cold receptor stimulus by 1-menthol are determined for each individual of the panel, the threshold for each individual being that amount of 1-menthol for which, in a series of not less than 10 test applications, a cooling effect is reported 50% of the time. Six panel members are now selected whose threshold to 1-menthol is in the range 0.1 $\mu$g to 10 $\mu$g and whose average threshold is approximately 0.25 $\mu$g., this select panel being regarded as the test panel of average sensitivity.

COMPOUND TESTING

To test the activity of compounds according to this invention, the above procedure is repeated using only the six selected panel members of average sensitivity to 1-menthol. The individual thresholds for each test compound on each of the six selected panel members are determined and averaged. Those compounds whose average threshold on the select test panel is 100 $\mu$g or less are regarded as having cooling activity in accordance with this invention.

TEST RESULTS

The following table sets out the relative cooling activities of compounds of the formula defined above when tested according to the foregoing procedure.

Table

| Compound | | Threshold |
|---|---|---|
| R' | R'' | $\mu$g. |
| H | $-CH_3$ | 1.1 |
| " | $-C_2H_5$ | 0.3 |
| " | $-C_3H_7(n)$ | 0.8 |
| " | $-C_3H_7(iso)$ | 0.5 |
| " | $-C_4H_9(n)$ | 1.4 |
| " | $-C_4H_9(iso)$ | 0.9 |
| " | $-C_4H_9(sec)$ | 0.7 |
| " | $-C_4H_9(tert.)$ | 0.4 |
| " | $-C_5H_{11}(n)$ | 3 |
| " | $-C_{10}H_{21}(n)$ | 10 |
| " | $-CH_2CH_2OH$ | 5 |
| " | $-(CH_2)_3OH$ | 3 |
| " | $-CH_2CH(OH)CH_3$ | 5.5 |
| " | $-C(CH_3)_2CH_2OH$ | 0.4 |
| " | $-CH_2c\equiv CCH_2OH$ | 17 |
| " | $-(CH_2)_6OH$ | 1.0 |
| " | $-CH(C_2H_5)CH_2OH$ | 1.0 |
| " | $-CH_2OH$ | 12 |
| " | $-CH_2COOC_3H_7(n)$ | 0.3 |
| " | $-CH_2COOC_2H_5$ | 0.2 |
| " | $-CH_2COOH$ | 16 |
| " | $-CH(CH_3)COOC_2H_5$ | 0.4 |
| " | $-CH_2CH_2COOC_2H_5$ | 1.5 |
| " | $-CH_2COOCH_3$ | 0.6 |
| " | $-CH(CH_3)CH_2COOC_2H_5$ | 0.8 |
| " | $-CH_2CH_2OCOCH_3$ | 1.5 |
| " | $-CH_2CH_2NH_2$ | 20 |
| $-CH_3$ | $-CH_3$ | 1.5 |
| $-C_2H_5$ | $-C_2H_5$ | 3 |
| $-CH_2CH_2OH$ | $-CH_2CH_2OH$ | 50 |
| $-CH_3$ | $-CH_2CO_2C_2H_5$ | 0.8 |
| $-CH_3$ | $-CH_2CH_2OH$ | 5 |
| $-C_3H_7(iso)$ | $-CH_2CH_2OH$ | 3 |
| H | $-C_3H_5(cyclo)$ | 0.5 |
| " | $-C_5H_9(cyclo)$ | 0.5 |
| " | $-C_6H_{11}(cyclo)$ | 1 |
| " | $-C_7H_{13}(cyclo)$ | 3 |
| $-C_2H_5$ | $-C_4H_9(iso)$ | 5 |
| H | $-CH_2(C_7H_{13})(cyclo)$ | 20 |
| H | $-OH$ | 11 |
| $-(CH_2)_4-$ | | 5 |
| $-(CH_2)_5-$ | | 6 |
| | $-CH_2CH_2OCH_2CH_2-$ | 5.5 |
| | $-CH_2CH_2NHCH_2CH_2$ | 15 |
| | $-CH(CH_3)CH_2CH_2CH(CH_3)-$ | 0.5 |
| | $-CH_2(CH_3)CH_2CH_2CH_2CH(CH_3)-$ | 2 |
| | $-CH(CH_3)CH(C_2H_5)CH_2C(CH_3)-$ | |
| | $-CH(iso-C_3H_7)CH_2CH_2CH(CH_3)CH_2CH_2-$ | 50 |
| H | $-CH_2Ph$ | 10 |
| " | $-C_6H_4OMe(p)$ | 0.1 |
| " | $-C_6H_4OH(p)$ | 1.4 |
| " | $-C_6H_4Me(p)$ | 0.3 |
| " | $-C_6H_4OH(o)$ | 0.5 |
| " | $-C_6H_3Me(p)OH(m)$ | 0.1 |
| " | $-C_6H_3Me_2(m,p)$ | 0.1 |
| " | $-C_6H_4F(p)$ | 0.5 |
| " | $-C_6H_4NO_2(p)$ | 0.3 |

Table-continued

| Compound | Threshold |
|---|---|
| -3-Pyridyl | 0.5 |

In formulating the tobacco and tobacco-containg manufactures of this invention the active compound may be incorporated directly into the tobacco, for example, by impregnation of the tobacco with an alcoholic solution of the active ingredient, at a suitable stage of manufacture. However, in an alternative and preferred arrangement, the active ingredient may be incorporated into a tobacco smoke filter for use in a pipe or cigarette filter or as a filter tip for cigarettes. The latter, in particular, forms a particularly effective utilisation of the present invention, the active compound simply being impregnated in the wad of material forming the filter tip. This may be of any of the well known types of filter tip for cigarettes, e.g. a filter pad of cellulose acetate, paper, cotton, α-cellulose or asbestos fiber. Conveniently the filter tip is impregnated with an alcoholic solution of the active compound and then dried to deposit the active compound therein.

The amount of active compound to be incorporated into the tobacco or tobacco-containing manufacture in accordance with the invention will vary from compound to compound depending on the activity thereof, i.e. the amount thereof which it is necessary to place in contact with the skin to produce a noticeable cooling effect, and will depend also on the mode of application thereof, i.e. whether the compound is impregnated in the tobacco itself, or in a filter tip or in any other accessory. However, the actual amount is not critical to this invention and will be readily determinable by the person skilled in the art by means of a few simple tests. As a matter of guidance, however, it may be mentioned that with the more active compounds, as little as 0.003 mg. deposited on the filter tip of a tipped cigarette is effective.

The invention is illustrated by the following Examples.

EXAMPLE 1

Cigarette Tobacco

A proprietary brand of cigarette tobacco was sprayed with an ethanolic solution of N,N-dimethyl-p-menthane-3-carboxamide and was rolled into cigarettes each containing approximately 5.0 micrograms of active compound. Smoking the impregnated cigarettes produced a cool effect in the mouth characteristic of mentholated cigarettes but without any attendant odour other than that normally associated with tobacco.

EXAMPLE 2

Filter Tip Cigarettes

The filter tip of a proprietary brand of cigarette was impregnated with an ethanolic solution of N-ethyl-p-menthane-3-carboxamide in an amount sufficient to deposit in the filter 0.003 mg. of the active compound. Smoking the cigarette with the impregnated tip gave rise to a noticeable cooling effect in the mouth.

EXAMPLE 3

Pipe Tobacco

A proprietary brand of pipe tobacco was sprayed with an ethanolic solution of N-t-tubyl-p-menthane-3-carboxamide 2g. of the tobacco, containing 8mg. of the active compound was placed in a pipe. Smoking the impregnated tobacco produced a cool effect in the mouth characteristic of mentholated tobacco but without any attendant odour other than that normally associated with tobacco.

EXAMPLE 4

Cigars

The tobacco of a proprietary brand of cigar was impregnated with an ethanolic solution of N-isopropyl-p-menthane-3-carboxamide in an amount sufficient to deposit in the cigar 2mg. of the active compound. Smoking the cigar with the impregnated tobacco gave rise to a noticeable cooling effect in the mouth.

EXAMPLE 5

Chewing Tobacco

A proprietary brand of chewing tobacco was impregnated with an ethanolic solution of N-(p-menth-3-oyl) glycine ethyl ester;1g. of the tobacco containing 0.5mg. of active compound was used. Chewing the impregnated tobacco produced a cool effect in the mouth.

EXAMPLE 6

Snuff

A proprietary brand of snuff was impregnated with an ethanolic solution of N-(p-menth-3-oyl) glycine n-propyl ester. 1g. of the snuff was impregnated with 4mg. of active compound. About 0.01g. of the impregnated snuff produced a cool effect in the nose when inhaled.

We claim:

1. A tobacco or tobacco-containing manufacture comprising tobacco and an agent capable of stimulating the cold receptors of the nervous system of the nasal or oral mucosa when brought into contact therewith upon use of the manufacture, wherein said agent comprises an effective amount of a cold receptor stimulating N-substituted p-methane carboxamide of the formula:

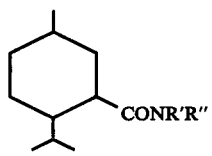

Where
R', when taken separately, is hydrogen or an aliphatic radical containing up to 25 carbon atoms and selected from alkyl, cycloalkyl, cycloalkylalkyl, hydroxyalkyl, alkynyl, hydroxyalkynyl, acyloxyalkyl, alkoxyalkyl, aminoalkyl, acylaminoalkyl, calboxyalkyl and alkylcarbonyalkyl;

R", when taking separately, is hydroxy, or an aliphatic radical containing up to 25 carbon atoms and selected from alkyl, cycloalkyl, cycloalkylalkyl, hydroxyalkyl, alkynyl, hydroxyalkynyl, acyloxyalkyl, alkylcarbonyalkyl, with the proviso that when R' is hydrogen R" may also be an aryl radical of up to 10 carbon atoms and selected from the group consisting of benzyl, pyridyl, and substituted phenyl wherein the substituents are selected from $C_1$-$C_4$ alkyl, hydroxy, $C_1$-$C_4$ alkoxy, nitro and halogen; and R' and R", when taken together with the nitrogen atom to which they are attached, represent a cyclic or heterocyclic group of up to 25 carbon atoms.

2. A manufacture according to claim 1, wherein said N-substituted-p-menthane carboxamide is of the formula defined, where R", when taken separately, is hydrogen, $C_1$-$C_9$ straight or branched chain alkyl, $C_1$-$C_9$ straight or branced chain hydroxyalkyl or aminoalkyl or a $C_1$-$C_4$ acylated derivative thereof, or —$C_nH_{2n}$COR'" or —$C_nH_{2n}$COOR'" where —$C_nH_{2n}$ is a straight or branched chain alkylene group in which $n$ is an integer of from 1-6 and R'" is hydrogen or $C_1$-$C_8$ alkyl or $C_1$-$C_8$ hydroxalkyl; R", when taken separately, is an organic group as defined above for R', R' and R" being the same of different; and R' and R", when taken together represent a alkylene chain optionally interrupted by oxygen and forming, together with the nitrogen atom to which R' and R" are attached, a 5- or 6-membered ring.

3. Manufactures according to claim 1, wherein said agent is of the formula defined where R' and R" are both alkyl of 1-3 carbon atoms.

4. Manufactures according to claim 1, wherein said agent is of the formula defined where R' is hydrogen and R" is alkyl of 1-3 carbon atoms, hydroxyalkyl of 1-4 carbon atoms or —$CH_2$COOR'", where R'" is alkyl of 1-4 carbon atoms.

5. A manufacture according to claim 1, wherein said agent is one of the following:

N-methyl-p-menthane-3-carboxamide;
N-ethyl-p-menthane-3-carboxamide;
N-t-butyl-p-menthane-3-carboxamide;
N-p-menth-3-oylglycine ethyl ester;
N-(1,1-dimethyl-2-hydroxy ethyl)-p-menthane-3-carboxamide;
N-p-menth-3-oylglycine-n-propyl ester.

6. Tobacco impregnated with an amount of a cold receptor stimulant effective to stimulate the cold receptors of the nervous system of the oral or nasal mucosa when said tobacco, or the smoke therefrom, is in contact therewith, wherein said stimulant is a cold receptor stimulating 3-substituted-p-menthane of the formula defined in claim 1.

7. A cigarette containing an amount of a cold receptor stimulant effective to stimulate the cold receptors of the nervous system of the oral or nasal mucosa when the cigarette is smoked, wherein said stimulant is a cold receptor stimulating 3-substituted-p-menthane of the formula defined in claim 1.

8. A filter-tipped cigarette comprising a filter tip, a tobacco-containing body, and an amount of a cold receptor stimulant effective to stimulate the cold receptors of the nervous system of the oral or nasal mucosa while the cigarette is smoked, wherein said stimulant is a cold receptor stimulating 3-substituted-p-menthane of the formula defined in claim 1 which is impregnated in said filter tip.

9. A method of stimulating the cold receptors of the nervous system of the nasal and oral mucosa which comprises contacting said mucosa with an effective amount of a cold receptor stimulating 3-substituted-p-menthane of the formula defined in claim 1, entrained in a stream of tobacco smoke.

10. A method of imparting to tobacco and tobacco-containing manufactures the property of stimulating the cold receptors of the nervous system of oral or nasal mucosa when in contact therewith, or when the smoke therefrom is inhaled, which comprises incorporating therein an effective amount of a cold receptor stimulating 3-substituted-p-menthane of the formula defined in claim 1.

* * * * *